(12) United States Patent
Hall et al.

(10) Patent No.: US 10,893,852 B2
(45) Date of Patent: *Jan. 19, 2021

(54) TOILET BOWL URINE MEASUREMENT INSTRUMENTS (71) Applicants: David R. Hall, Provo, UT (US); Dan Allen, Springville, UT (US); Joe Fox, Spanish Fork, UT (US)

(72) Inventors: David R. Hall, Provo, UT (US); Dan Allen, Springville, UT (US); Joe Fox, Spanish Fork, UT (US)

(73) Assignee: Hall Labs, LLC, Provo, UT (US)

( * ) Notice: Subject to any disclaimer, the term of this patent is extended or adjusted under 35 U.S.C. 154(b) by 132 days.

This patent is subject to a terminal disclaimer.

(21) Appl. No.: 15/264,989

(22) Filed: Sep. 14, 2016

(65) Prior Publication Data
US 2018/0070926 A1 Mar. 15, 2018

(51) Int. Cl.
*A61B 10/00* (2006.01)
*G01N 33/493* (2006.01)
*A61B 5/20* (2006.01)
*G01N 21/21* (2006.01)
*G01N 21/41* (2006.01)
*G01N 21/51* (2006.01)
*A61B 5/1455* (2006.01)
(Continued)

(52) U.S. Cl.
CPC .......... *A61B 10/007* (2013.01); *A61B 5/1455* (2013.01); *A61B 5/207* (2013.01); *A61B 5/6891* (2013.01); *G01N 21/21* (2013.01); *G01N 21/251* (2013.01); *G01N 21/4133* (2013.01); *G01N 21/51* (2013.01); *G01N 33/493* (2013.01); *A61B 5/0075* (2013.01); *A61B 5/14532* (2013.01); *A61B 5/14558* (2013.01); *A61B 5/7203* (2013.01); *A61B 5/7228* (2013.01); *E03D 11/025* (2013.01); *E03D 2201/40* (2013.01); *G01N 15/0211* (2013.01); *G01N 2015/0053* (2013.01); *G01N 2015/0693* (2013.01)

(58) Field of Classification Search
CPC ... A61B 10/007; A61B 5/6887; A61B 5/6891; A61B 5/207; G01N 33/493; G01N 33/48707
See application file for complete search history.

(56) References Cited

U.S. PATENT DOCUMENTS 2,559,688 A * 7/1951 Touvet ............... G01J 3/10 250/575
3,155,762 A * 11/1964 Gillham ............. G01J 3/42 356/327
(Continued)

FOREIGN PATENT DOCUMENTS

JP 08226160 A * 9/1996
JP 2000310635 A * 11/2000

OTHER PUBLICATIONS

Google Patents English Translation of JP 08226160 A.*

*Primary Examiner* — Thaddeus B Cox (57) ABSTRACT

A toilet with multiple urinalysis instruments is disclosed. Two or more of the optical instruments are able to take simultaneous measurements. Optical instruments may share a common light source. One or more light source may use amplitude modulation. A cleaning jet may be used to clean and dry a surface tension urine slot. An inductive heater may be used to preheat and control urine temperature while testing the urine.

19 Claims, 10 Drawing Sheets (51) Int. Cl.
*A61B 5/00* (2006.01)
*G01N 21/25* (2006.01)
*G01N 15/00* (2006.01)
*G01N 15/02* (2006.01)
*A61B 5/145* (2006.01)
*G01N 15/06* (2006.01)
*E03D 11/02* (2006.01)

(56) References Cited

U.S. PATENT DOCUMENTS

| | | | | | |
|---|---|---|---|---|---|
| 4,356,396 | A | * | 10/1982 | Ruell | G01D 5/30 250/226 |
| 4,444,148 | A | * | 4/1984 | Lander | A01K 1/0107 119/161 |
| 5,111,539 | A | * | 5/1992 | Hiruta | A61B 5/02241 4/301 |
| 5,164,954 | A | * | 11/1992 | Su | H01S 5/1071 372/20 |
| 6,426,045 | B1 | * | 7/2002 | Jeng | G01N 21/05 356/246 |
| 2004/0146428 | A1 | * | 7/2004 | Minter | A61B 10/007 422/412 |
| 2007/0171413 | A1 | * | 7/2007 | Vannuffelen | G01J 3/0218 356/328 |
| 2009/0216099 | A1 | * | 8/2009 | Kim | A61B 5/022 600/345 |
| 2015/0342574 | A1 | * | 12/2015 | Hall | A61B 10/007 600/573 |
| 2015/0359522 | A1 | * | 12/2015 | Recht | G01N 33/62 600/573 |
| 2016/0000378 | A1 | * | 1/2016 | Hall | A61B 5/0075 702/19 |
| 2019/0017994 | A1 | * | 1/2019 | Tsuruoka | G01N 27/06 |

* cited by examiner

TOILET BOWL URINE MEASUREMENT INSTRUMENTS

BACKGROUND

Field of the Invention

The present invention relates to the function and utility of in-toilet urine capture and measurement.

Background of the Invention

Urinalysis is a cheap, fast and simple screening tool for many health conditions. The urinalysis machine is large and expensive and inconvenient for users (pee in a cup). A method for analyzing urine, providing a variety of health-relevant measurements in a toilet is needed.

SUMMARY

This invention has been developed in response to the present state of the art and, in particular, in response to the problems and needs in the art that have not yet been fully solved by currently available systems and methods. Accordingly, a toilet bowl with multiple urine measurement instruments has been developed. Features and advantages of different embodiments of the invention will become more fully apparent from the following description and appended claims, or may be learned by practice of the invention as set forth hereinafter.

According to the invention, a toilet bowl with a recess which traps urine is in optical communication with a plurality of optical instruments that provide simultaneous measurements of the trapped urine in the recess. The plurality of optical instrument may include refractometers, spectrometers, glucose polarimeters, laser scatterometers, turbidity detectors, and microscopes. The plurality of optical instruments may comprise a refractometer, a spectrometer, a glucose polarimeter, and a turbidity detector. One or more of the plurality of optical instruments may comprise an amplitude modulated light source. The plurality of optical instruments may share one or more light sources. The recess may comprise a trap region that traps urine. The trap region may use surface tension to trap the urine. The trap region may comprise a longitudinal dimension in a longitudinal direction and a transverse dimension in an orthogonal transverse direction, the longitudinal dimension being at least twice the transverse dimension. Two or more of the plurality of optical instruments may share an amplitude modulated light source. The recess may form a slit, groove, indentation, trench, pattern, divot, concavity, prism, lens, lens array, or diffraction grating. The recess may comprise a hydrophobic surface coating or a hydrophilic surface coating. The toilet may comprise a cleaning jet which cleans the recess. The cleaning jet may be located above the recess. The cleaning jet may spray water, air, cleaning solution, or a combination thereof to clean and dry the recess. A cleaning solution may be used in combination with water, air, or a combination of water and air to clean the recess. The recess may comprise a temperature sensor. The temperature sensor may be used to detect the urine entering the recess and to control a temperature of the recess. Two or more of the plurality of optical instruments may share an optical path through the urine. A common light source may be used in multiple light paths through urine by more than one optical instrument. The toilet may comprise a beam splitter. The beam splitter may be a polarization beam splitter or a non-polarization beam splitter. A polarization beam splitter and a non-polarization beam splitter may be used by one or more optical instruments. A polarization beam splitter and a non-polarization beam splitter may be located on a common optical axis. One or more controllers may be operably connected to one or more optical instruments. The one or more controllers may comprise a wireless or wired transceiver. The toilet may comprise a heater in thermal communication with the urine recess. One or more of the plurality of optical instruments may be glued to a surface of the bowl. The surface may be an interior surface or exterior surface of the bowl.

In an example, a collimated polarized light source, such as laser light collimated from a single mode fiber passes through the urine trapped in a recess. The beam may be divided by a non-polarizing beam-splitters and sent to a microscope objective to relay the beam to a camera for heterodyne near field light scattering measurements, useful for determining the particle size distribution in the urine. Hemoglobin, leukocytes and oxalate crystals are quite different in size and arise from different health conditions (kidney damage, urinary tract infection and kidney stone problems, respectively, for an example. The light scattering instrument path is bent downward by the beam splitter to create more space for the potentially bulky objective lens. Part of the laser beam may pass to a polarizing beam splitter allowing a differential measurement of the polarization state of the laser, which will depend on the glucose concentration, primarily. A differential measurement is particularly sensitive to small changes in polarization state and is suitable for shorter path length measurements than typical polarimeters which use 10 cm path length. A refractometer may be constructed from an LED, an optional aperture, an optical coupling element such as a prism and a detector with spatial resolution such as a segmented photodiode, position sensitive photodiode or camera. A range of incident angles may strike the urine from the bottom. Some rays totally internally reflect and create a bright portion on a detector. Other rays partially transmit and provide a lower level of illumination. A polarizer can optionally be included for better resolution. A refractometer may be oriented such the light path is in the plane of the long direction of the slit, rather than a short direction with advantages for optical alignment. A camera may also be used to detect scattered light from a laser, for measuring turbidity. A multi-wavelength light source and wavelength-sensitive detection can be included for spectroscopic or color measurements, as described hereinafter. A microscope may be used to accomplish microscopic analysis of the urine. Optical instruments may share a light source with homodyne near field scattering. Detectors may be masked photodiodes or (CCD, LCOS, CMOS) cameras when discrimination against a split out light path is desired. For robustness the entire optical assembly may be cemented together.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

A detailed description of the claimed invention is provided below by example, with reference to embodiments in the appended figures. Those of skill in the art will recognize that the components of the invention as described by example in the figures below could be arranged and designed in a wide variety of different configurations. Thus, the detailed description of the embodiments in the figures is merely representative of embodiments of the invention, and is not intended to limit the scope of the invention as claimed.

In some instances, features represented by numerical values, such as dimensions, mass, quantities, and other properties that can be represented numerically, are stated as approximations. Unless otherwise stated, an approximate value means "correct to within 50% of the stated value." Thus, a length of approximately 1 inch should be read "1 inch+/−0.5 inch."

Aspects of the present invention are described herein with reference to flowchart illustrations and/or block diagrams of methods, apparatus (systems), and computer program products according to embodiments of the invention. Those of skill in the art will understand that each block of the flowchart illustrations and/or block diagrams, and combinations of blocks in the flowchart illustrations and/or block diagrams, may be implemented by computer readable program instructions. Additionally, those of skill in the art will recognize that the system blocks and method flowcharts, though depicted in a certain order, may be organized in a different order and/or configuration without departing from the substance of the claimed invention.

Figure 1:
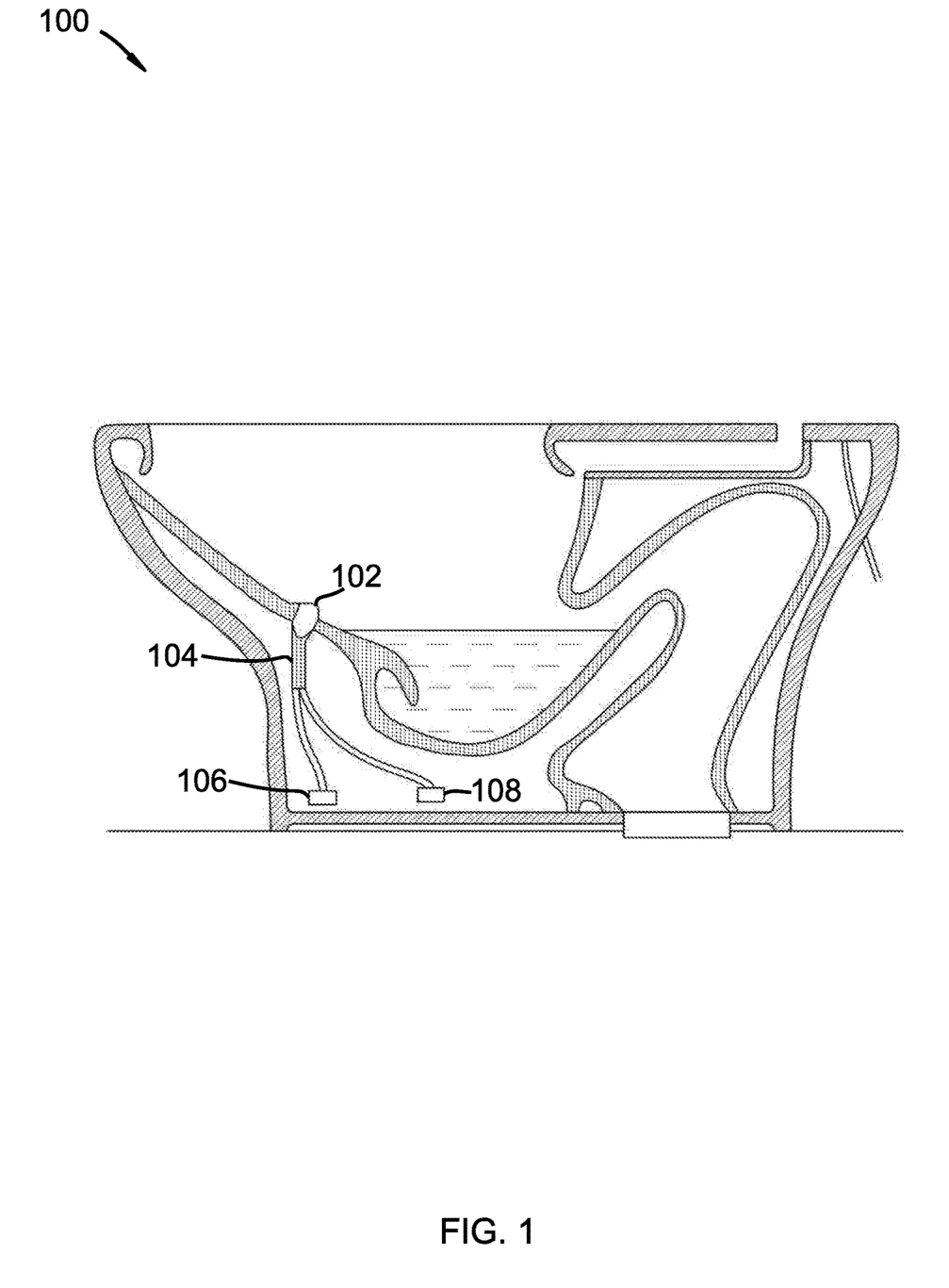
FIG. 1 shows a toilet bowl with urine measurement instruments.

Referring to FIG. 1, a toilet bowl 100 with urine measurement instruments 106 and 108 is depicted with a longitudinal raised urine barrier with a urine trapping recess area 102 and communication lines 104. Urine behind the barrier is pulled by gravity into the urine trapping recess area 102. Measurement instruments 106 and 108 may comprise refractometers, spectrometers, glucose polarimeters, laser scatterometers, turbidity detectors, and/or microscopes. Measurement instruments 106 and 108 may each contain one or more controllers, processors, light sources, lenses, diffraction optics, collimating optics, power sources, and light detectors. Power sources may be battery power, generator power, or a wired power connection. Each controller may contain wireless and wired transceivers for communicating data to remote computers, user devices, and remote databases. Data may be communicated over the Internet or over local networks and devices. Urine trapping recess area 102 may be formed in the barrier by a slit, groove, recess, indentation, trench, pattern, divot, concavity, prism, lens, lens array, and/or diffraction grating. Communication lines 104 may comprise wires or fiber optic lines.

Toilet bowl urine measurements may be taken when a toilet user urinates in toilet 100 and urine contacts the longitudinal urine barrier then enters the urine trapping area 102. The urine may directly hit trapping area 102 as released by a toilet user or the urine may travel along an inside surface of toilet 100 and become trapped in area 102. A temperature sensor located in trapping area 102 may detect urine and trigger measurement devices 106 and 108 to measure urine trapped in area 102. An inductive heater may be positioned within or near trapped area 102. A toilet controller may preheat area 102 and keep area 102 at a fixed temperature while performing urine testing. When measurements are complete, flush water released from toilet 100 may be used to clean trapped urine in area 102. The cleaning jet may be located above the recess. A cleaning jet may spray water, air, cleaning solution, or a combination thereof to clean and dry the recess. A cleaning solution may be used in combination with water, air, or a combination of water and air to clean the recess. A toilet controller may contain programming to wait for measurement devices 106 and 108 to complete urine measurements before allowing the toilet to flush. For example, a user may push the flush button and a toilet controller may delay the flush until it receives acknowledgement that the urine measurements are complete.

Figure 2:
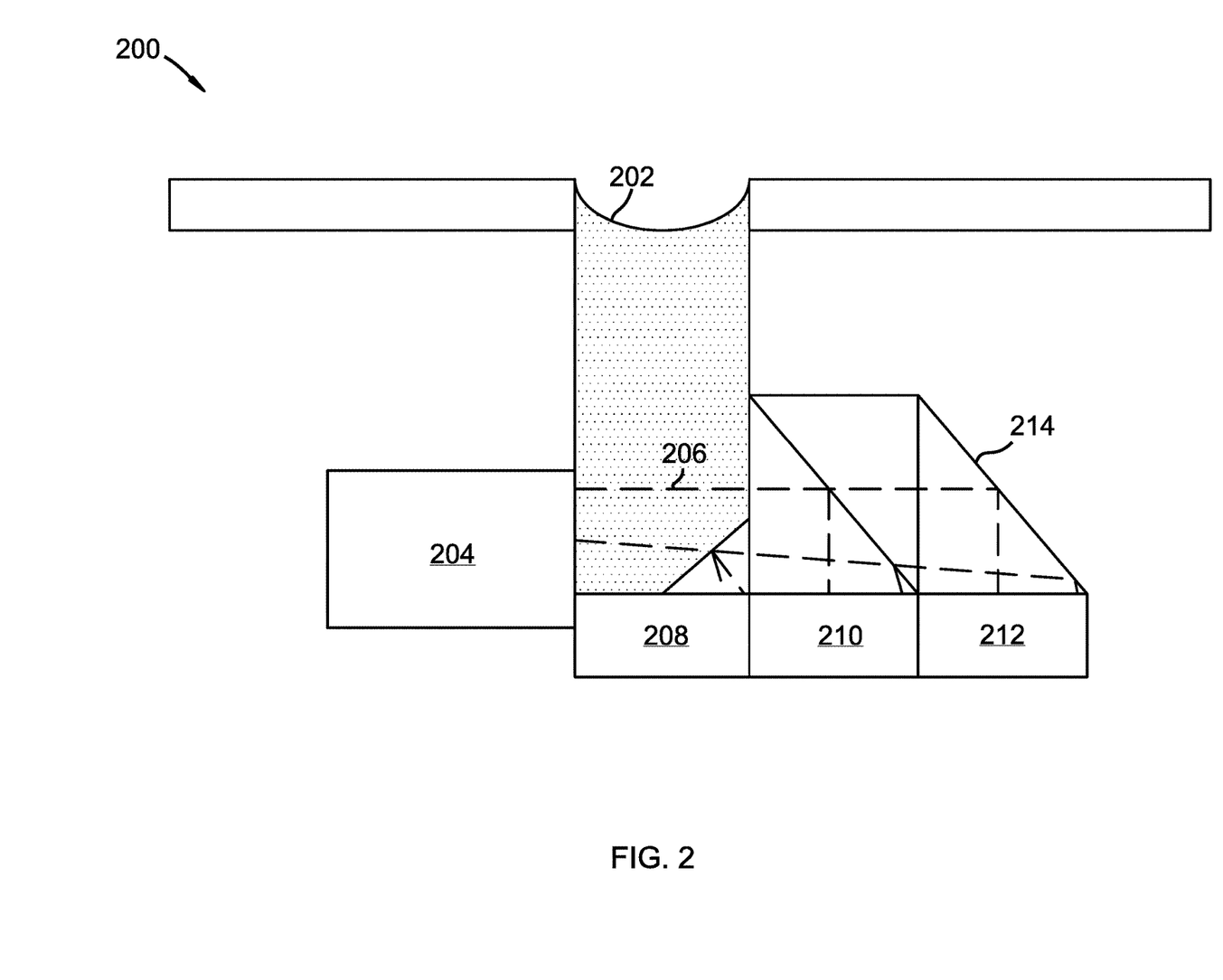
FIG. 2 shows an optical arrangement according to an embodiment of the invention.

FIG. 2 shows an optical measurement arrangement including urine 202 in a recess, with refractometer 208, turbidity sensor 208, light scattering particle sizer 208, glucose polarimeter 210/212/214, and a single shared light source 204. The recess that houses urine 202 may be formed by a slit in an optically transparent material such as glass, quartz, or plastics. Light source 204, refractometer detector 208, and glucose polarimeter detectors 210/212, or beam splitter 214 may entirely or partially form the recess. A polarized light source 204 may be a collimated laser, multiple collimated lasers of different frequency, one or more laser diodes, or a white light source which is polarized and collimated. One or more of the plurality of optical instruments may comprise an amplitude modulated light source. The amplitude modulated light source may be used to filter out noise, ambient noise, and to multiplex multiple optical data measurement signals of similar and dissimilar light sources. For instance, one or more light sources may be modulated on an off, or by amplitude modulation allowing noise to be separated from signal data.

When urine enters the recess, a temperature sensor within refractometer 208 may detect a temperature change and send a signal to a controller (not shown) to start measuring the urine in the slot. The light source 204 may then be activated and start transmitting light through urine 202. As light passes through urine 202, light is refracted, reflected, and rotated.

Polarimeter detectors 210 and 212 may be used to detect intensity and wavelength of polarization states which are orthogonal to each other. Beam splitter 214 may serve as a polarization beam splitter and separate polarization states which are orthogonal to each other, reflecting the different polarization states respectively to each detector 210 and 212. Beam splitter 214 may be a cube beam splitter employing thin films or a wire-grid polarizer. Beam splitter 214 may also use silvered mirrors and/or thin film interfaces to reflect light. Scattered, reflected and refracted light wavelength and intensity may be detected by a light detector within refractometer detector 208. A controller may be operably connected to detectors 208, 210, 212 and light source 204.

Measurement instruments 200 may contain one or more controllers, processors, light sources, lenses, diffraction optics, collimating optics, power sources, and light detectors. Power sources may be battery power, generator power, or a wired power connection. Each controller may contain wireless and wired transceivers for communicating data to remote computers, user devices, and remote databases. Data may be communicated over the Internet or over local networks and devices. The urine 202 trapping recess area may be formed by a slit, groove, recess, indentation, trench, pattern, divot, concavity, prism, lens, lens array, and/or diffraction grating.

Figure 3:
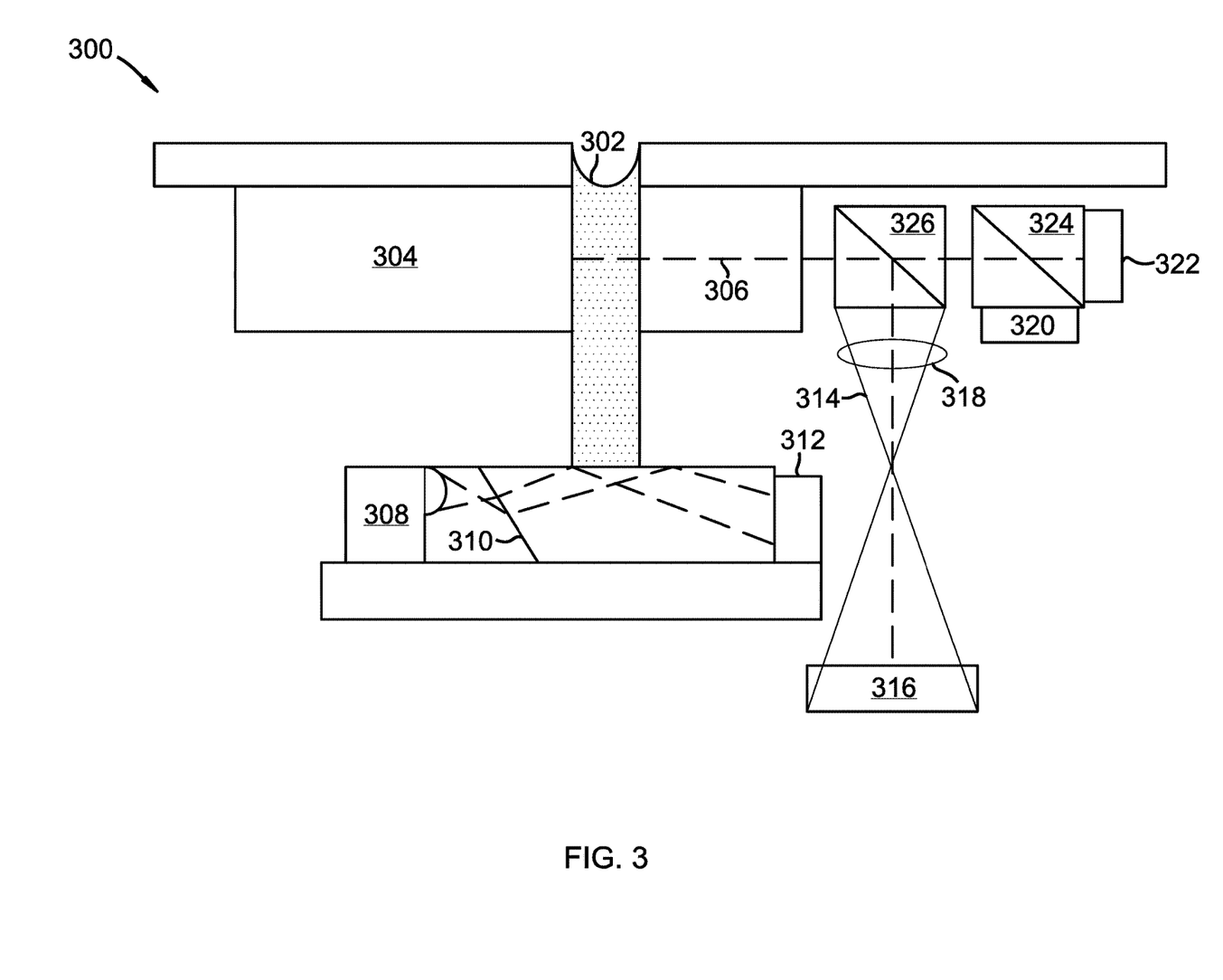
FIG. 3 shows an optical arrangement according to an embodiment of the invention.

FIG. 3 shows an optical arrangement according to an embodiment of the invention. Light source 304 may transmit polarized light 306 through urine 302. Beam splitter 326 is a non-polarization beam splitter such as a 50% silvered mirror or a thin film filter. Polarization beam splitter 324 and non-polarization beam splitter 326 are located on a common optical axis 306. When polarized light 306 is incident on beam splitter 326, 50% is transmitted to polarization beam splitter 324 to detectors 322 and 320 and 50% is reflected through lens 318 to detector 316. Detectors 320 and 322 may be used as part of a glucose polarimeter. Polarization rotation change as a result of light 306 passing through urine 302 can be detected by detectors 320 and 322. Detector 316 is used to detect particle size. Detectors 320, 322, 316 may be pixelated sensor arrays such as LCOS (liquid crystal on silicon), CMOS (complementary metal-oxide-semiconductor), CCD (capacitive coupled display), or arrays of photodiodes.

A refractometer comprising a light source 308, an aperture prism 310 and detector 312 may be positioned so the light transmitted from light source 308 is transmitted perpendicularly (the long direction of urine slot) to the light transmitted by light source 304. FIG. 3 shows refractometer 308, 310, and 312 in the same plane as 304, but the refractometer system may be coming out of the page in the "z" direction. Transmitting and detecting light in the long direction saves space and also provides more cross-sectional area for refractometer and turbidity measurements.

Measurement instruments 300 may contain one or more controllers, processors, light sources, lenses, diffraction optics, collimating optics, power sources, and light detectors. Power sources may be battery power, generator power, or a wired power connection. Each controller may contain wireless and wired transceivers for communicating data to remote computers, user devices, and remote databases. Data may be communicated over the Internet or over local networks and devices. The urine 302 trapping recess area may be formed by a slit, groove, recess, indentation, trench, pattern, divot, concavity, prism, lens, lens array, and/or diffraction grating.

Figure 4:
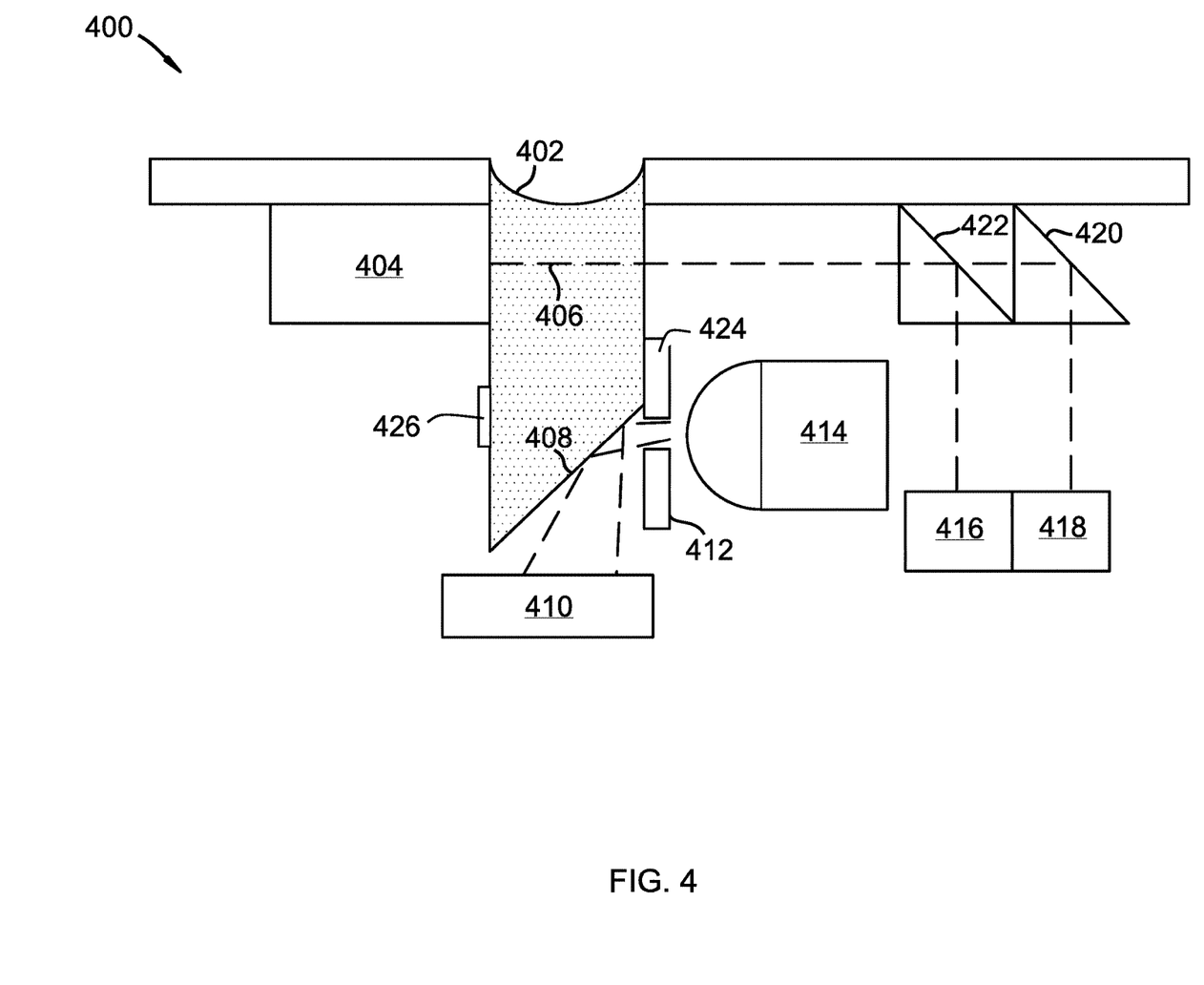
FIG. 4 shows an optical arrangement according to an embodiment of the invention.

FIG. 4 shows an optical measurement arrangement including urine 402 in a recess, with refractometer detector 410, dynamic light scattering detector 410, turbidity sensor 410, light scattering particle sizer 410, color sensor 410, glucose polarimeter detectors 416/418, and beam splitters 422 and 420. The recess that houses urine 402 may be formed by a slit in an optically transparent material such as glass, quartz, or plastics. Light source 404, refractometer detector 410, dynamic light scattering detector 410, turbidity sensor 410, light scattering particle sizer 410, color sensor 410, glucose polarimeter detectors 416/418, and beam splitters 422 and 420 may entirely or partially form the recess. Light sources 404 and 414 may be a collimated laser, multiple collimated lasers of different frequency, one or more laser diodes, or a white light source which is polarized and collimated. Surface 408 may be formed as part of a prism and used to assist in reflection of light from light source 414 to detector 410. Detectors 410, 418, 416 may be pixelated sensor arrays such as LCOS (liquid crystal on silicon), CMOS (complementary metal-oxide-semiconductor), CCD (capacitive coupled display), or arrays of photodiodes. Beam splitter 422 may serve as a polarization beam splitter and separate polarization states which are orthogonal to each other, reflecting the different polarization states respectively to each detector 416 and 418. Beam splitter 422 may be a cube beam splitter employing thin films or a wire-grid polarizer. Beam splitter 420 may use a silvered mirror and/or thin film interfaces to reflect light. A heater 424, may be used to heat or preheat urine trapping area or urine 402. The heater 424 may be a resistive or inductive heater. A temperature sensor 426 may be used to detect urine 402 entering the recess and also may be used in combination with heater 424 to control temperature of the urine while measuring the urine. Temperature sensor 426 and heater 424 may be used to preheat the urine trap recess area before testing.

Measurement instruments 400 may contain one or more controllers, processors, light sources, lenses, diffraction optics, collimating optics, power sources, and light detectors. Power sources may be battery power, generator power, or a wired power connection. Each controller may contain wireless and wired transceivers for communicating data to remote computers, user devices, and remote databases. Data may be communicated over the Internet or over local networks and devices. The urine 402 trapping recess area may be formed by a slit, groove, recess, indentation, trench, pattern, divot, concavity, prism, lens, lens array, and/or diffraction grating.

Figure 5:
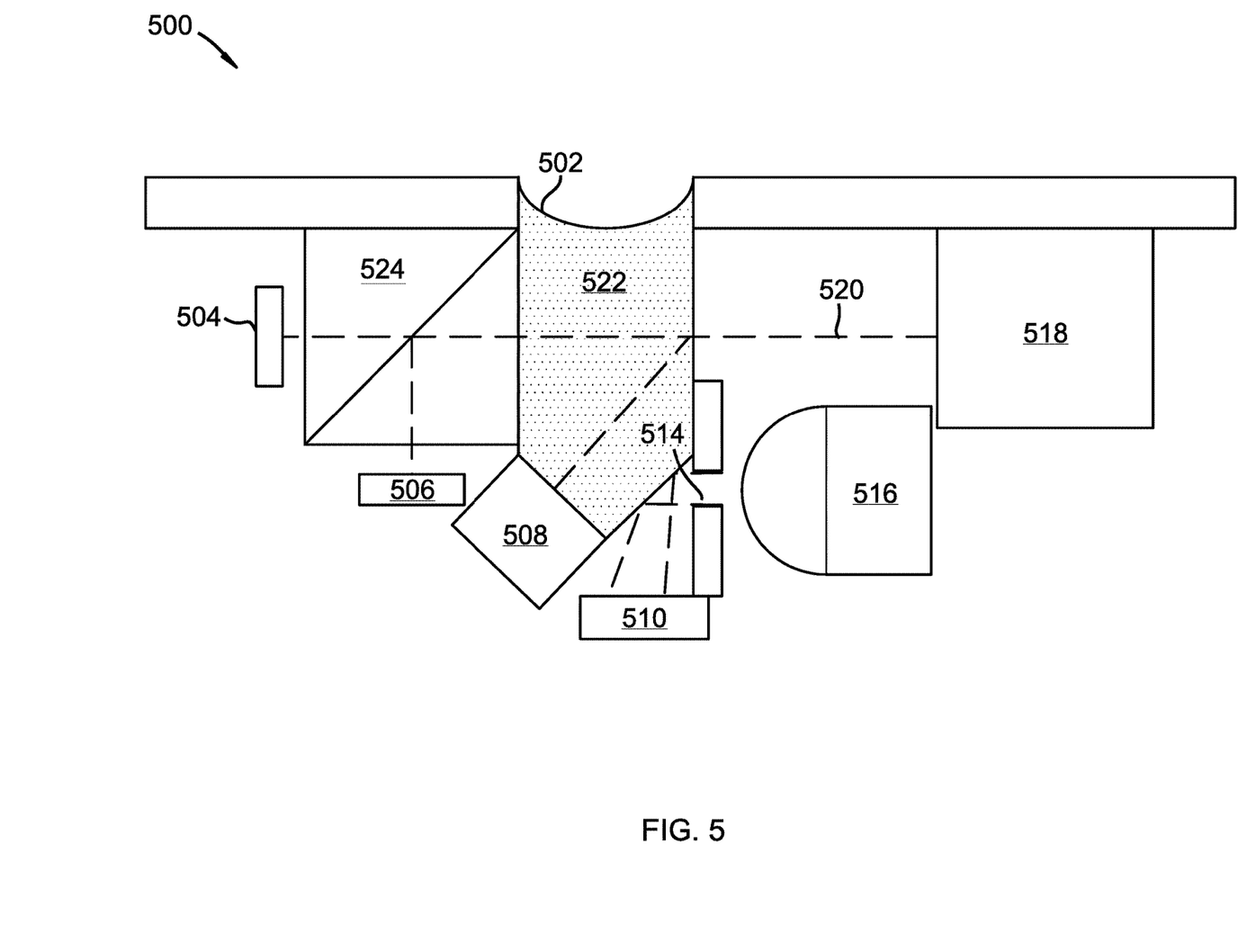
FIG. 5 shows an optical arrangement according to an embodiment of the invention.

FIG. 5 shows an optical measurement arrangement including urine 502 in a recess, with refractometer detector 510, dynamic light scattering detector 510, turbidity sensor 510, light scattering particle sizer 510, color sensor 510, glucose polarimeter detectors 504/506, and beam splitter 524. The recess 522 that houses urine 502 may be formed by a slit in an optically transparent material such as glass, quartz, or plastics. Light source 518, refractometer detector 510, dynamic light scattering detector 510, turbidity sensor 510, light scattering particle sizer 510, color sensor 510, glucose polarimeter detectors 504/506, and beam splitter 524 may entirely or partially form the recess. Light sources 518, 516 and 508 may be a collimated laser, multiple collimated lasers of different frequency, one or more laser diodes of different frequencies, or a white light source which is polarized and collimated. Detectors 510, 504, 506 may be pixelated sensor arrays such as LCOS (liquid crystal on silicon), CMOS (complementary metal-oxide-semiconductor), CCD (capacitive coupled display), or arrays of photodiodes. Beam splitter 524 may serve as a polarization beam splitter and separate polarization states which are orthogonal to each other, reflecting the different polarization states respectively to each detector 504 and 506. Beam splitter 524 may be a cube beam splitter employing thin films or a wire-grid polarizer.

Measurement instruments 500 may contain one or more controllers, processors, light sources, lenses, diffraction optics, collimating optics, power sources, and light detectors. Power sources may be battery power, generator power, or a wired power connection. Each controller may contain wireless and wired transceivers for communicating data to remote computers, user devices, and remote databases. Data may be communicated over the Internet or over local networks and devices. Urine trapping recess area 522 may be formed by a slit, groove, recess, indentation, trench, pattern, divot, concavity, prism, lens, lens array, and/or diffraction grating.

Figure 6:
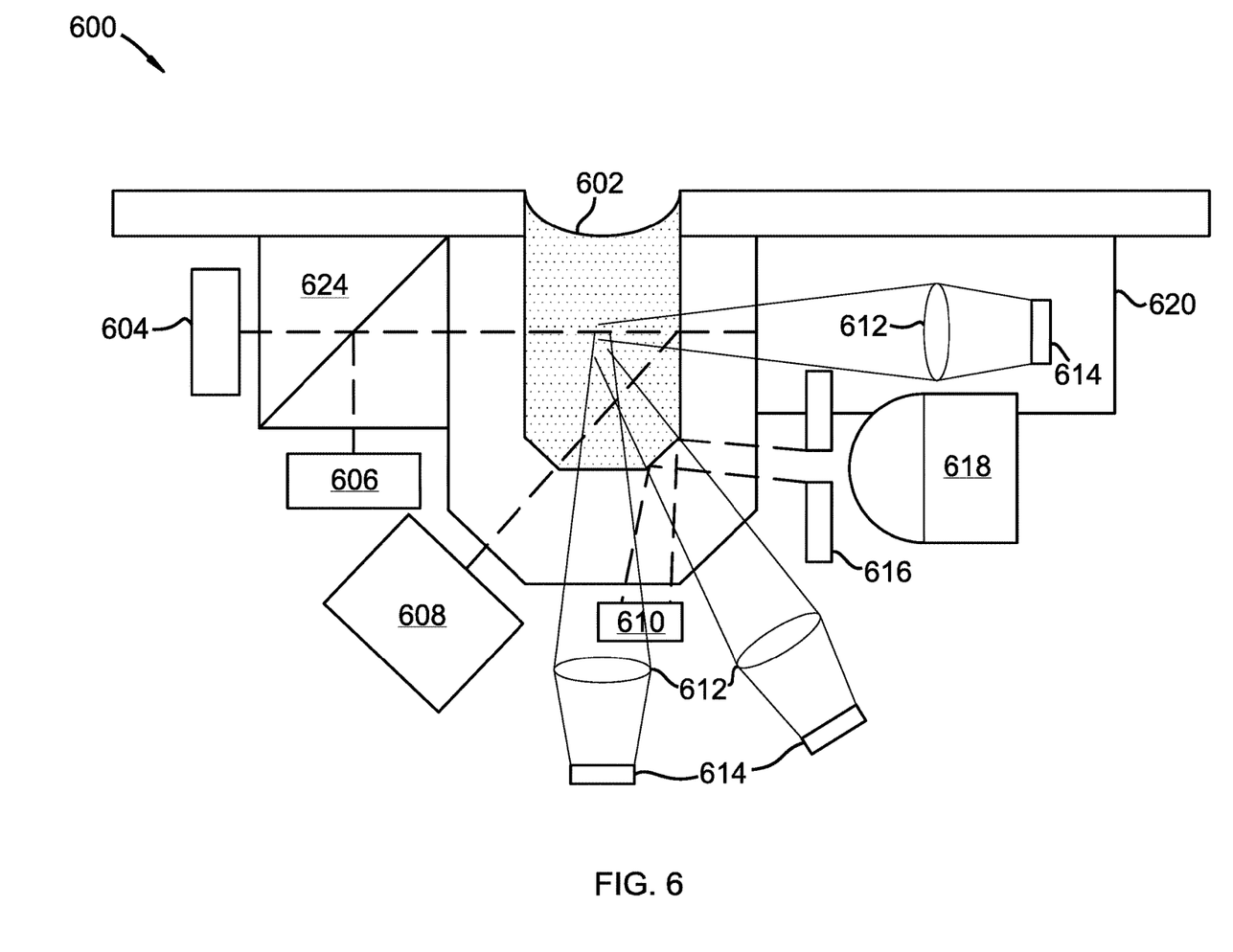
FIG. 6 shows an optical arrangement according to an embodiment of the invention.

FIG. 6 shows an optical measurement arrangement including urine 602 in a recess, with refractometer detector 610, dynamic light scattering detectors 614, turbidity sensors 614, light scattering particle sizers 614, color sensors 614, glucose polarimeter detectors 604/606, and beam splitter 624. The recess that houses urine 602 may be formed by a slit in an optically transparent material such as glass, quartz, or plastics. Light sources 620, 614, 618, and 608, refractometer detector 610, dynamic light scattering detector 614, turbidity sensor 614, light scattering particle sizer 614, color sensor 614, glucose polarimeter detectors 604/606, and beam splitter 624 may entirely or partially form the recess. Light sources 620, 614, 618, and 608 may be a collimated laser, multiple collimated lasers of different frequency, one or more laser diodes of different frequencies, or a white light source which is polarized and collimated. Multi-angle, multiple wavelength measurements are enabled as a result of detectors 614 and multiple wavelength light source 608. Detectors 610, 614, 606, and 604 may be pixelated sensor arrays such as LCOS (liquid crystal on silicon), CMOS (complementary metal-oxide-semiconductor), CCD (capacitive coupled display), or arrays of photo-diodes. Beam splitter 624 may serve as a polarization beam splitter and separate polarization states which are orthogonal to each other, reflecting the different polarization states respectively to each detector 604 and 606. Beam splitter 624 may be a cube beam splitter employing thin films or a wire-grid polarizer. Lenses 612 are used to focus varying depths of the urine 602 on detectors 614. Lens 612 is a collimating lens which collimates light source 614. Light source 620 is a collimated polarized light source. 616 is a aperture for directing light onto detector 610.

Measurement instruments 600 may contain one or more controllers, processors, light sources, lenses, diffraction optics, collimating optics, power sources, and light detectors. Power sources may be battery power, generator power, or a wired power connection. Each controller may contain wireless and wired transceivers for communicating data to remote computers, user devices, and remote databases. Data may be communicated over the Internet or over local networks and devices. The urine trapping recess area may be formed by a slit, groove, recess, indentation, trench, pattern, divot, concavity, prism, lens, lens array, and/or diffraction grating.

Figure 7:
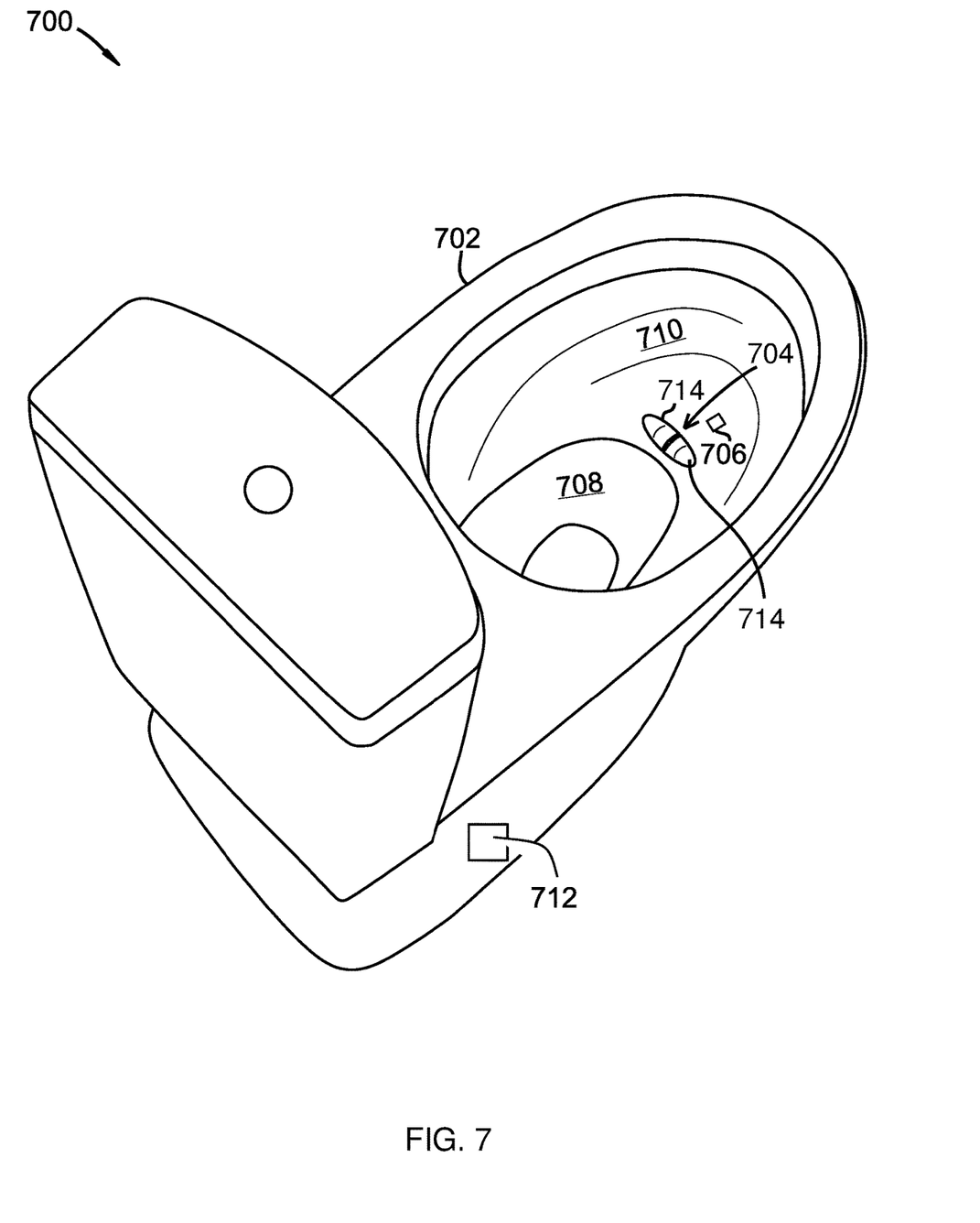
FIG. 7 shows a toilet bowl with a urine recess trap according to an embodiment of the invention.

FIG. 7 shows a toilet 700 including a toilet bowl 702, an inner surface 710 of the toilet bowl, a longitudinal raised urine barrier 714 with an orthogonal recessed urine trapping device 704 traversing the barrier, a cleaning jet 706, a toilet controller 712, and bowl water 708. Longitudinal raised urine barrier 714 and recessed urine trapping device 704 are located above bowl water 708 and still low enough to trap urine in a slot in recessed urine trapping device 704. The slot may comprise a trap region that traps urine via surface tension. The trap region may comprise a longitudinal dimension in a longitudinal direction and a transverse dimension in an orthogonal transverse direction, the longitudinal dimension being at least twice the transverse dimension. The cleaning jet may be operably connected to a toilet controller 712 and a solenoid valve. The controller 712 may be programmed to actuate one or more solenoids allowing air, water, or a combination of air and water to spray a jet stream into the urine trap area effectively cleaning the urine out of the trap area and leaving the trap area dry. The controller 712 may alternate cleaning and drying of the trap area for a predetermined number of iterations such as 5 or 10.

Figure 8:
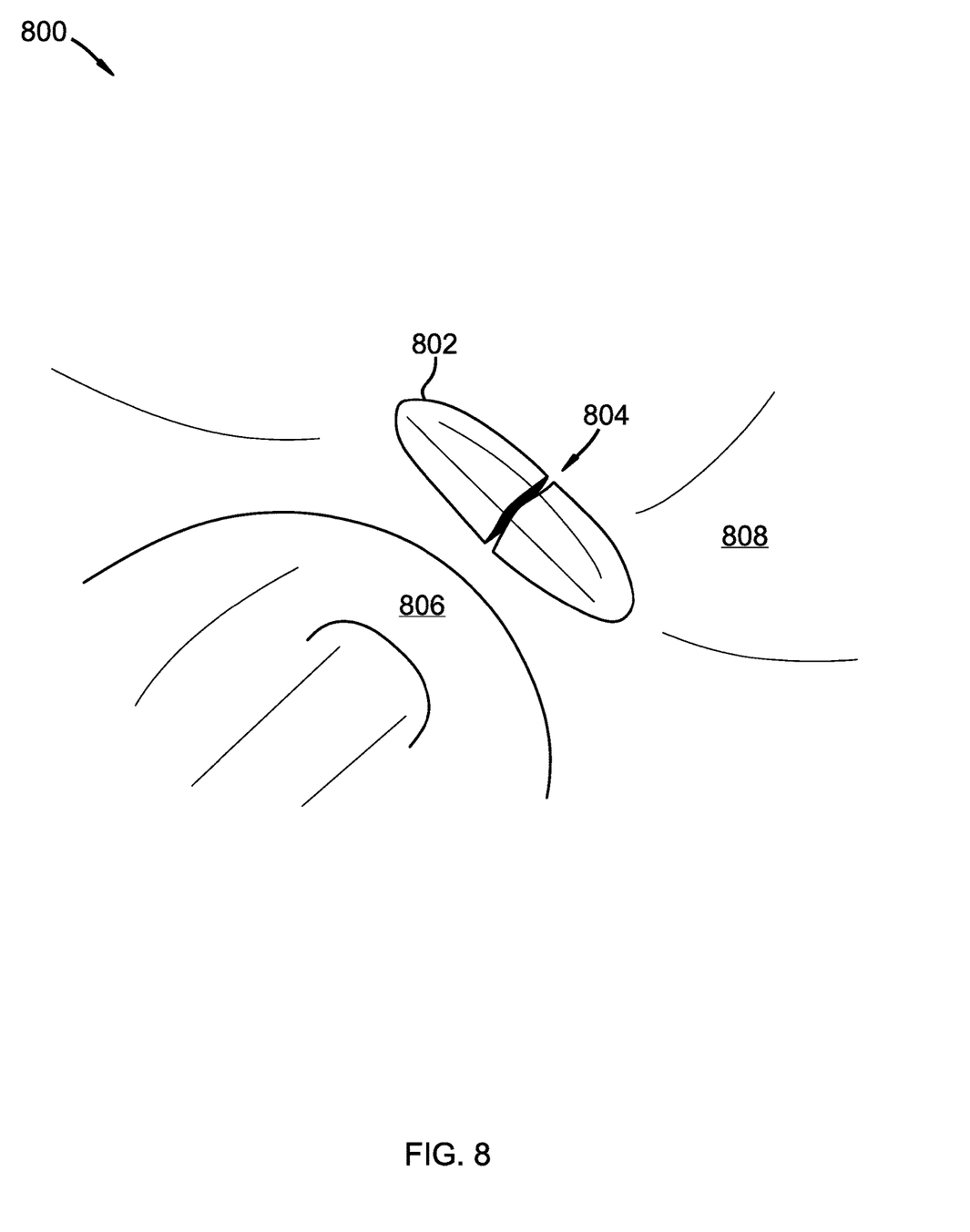
FIG. 8 shows a toilet bowl with a urine recess trap according to an embodiment of the invention.

FIG. 8 shows a toilet 800 including a toilet bowl, an inner surface 808 of the toilet bowl, a longitudinal raised urine trapping barrier 802, a recessed slot 804 in barrier 802, and bowl water 806. The longitudinal raised urine trapping barrier 802 is located above bowl water 806 and still low enough to trap urine in a slot in urine trapping barrier 802. The recessed slot 804 may comprise a trap region that traps urine via surface tension. The trap region may comprise a longitudinal dimension in a longitudinal direction and a transverse dimension in an orthogonal transverse direction, the longitudinal dimension being at least twice the transverse dimension. When urine measurements are complete, flush water release from toilet 800 may be used to clean trapped urine in area recessed slot 804. A toilet controller may contain programming to wait for urine measurement devices to complete urine measurements before allowing the toilet to flush. For example, a user may push the flush button and a toilet controller may delay the flush until it receives acknowledgement that the urine measurements are complete.

Figure 9:
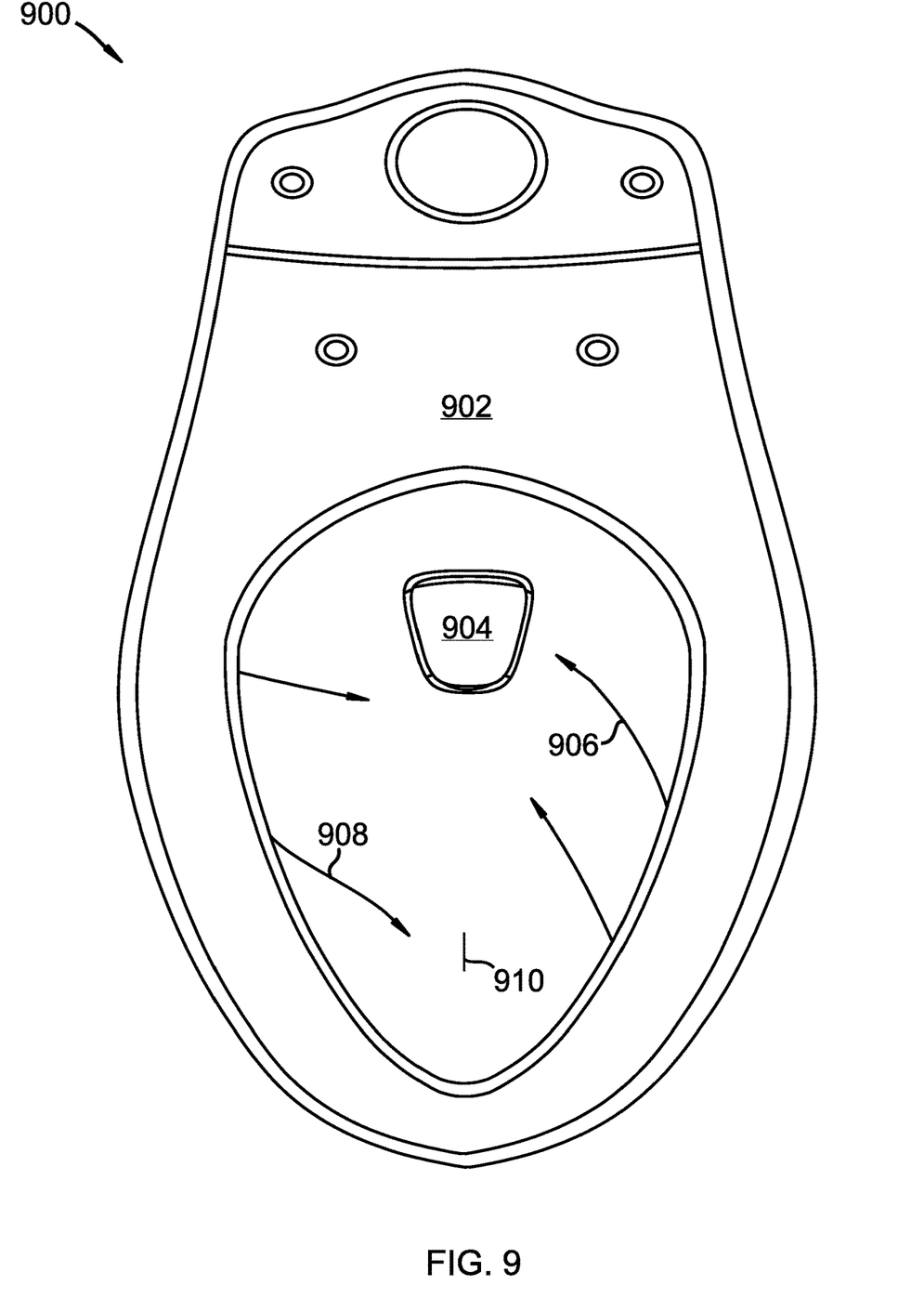
FIG. 9 shows a toilet bowl with a urine recess trap according to an embodiment of the invention.

FIG. 9 shows a toilet 900 including a toilet base 902, water patterns 906 and 908 of the toilet base, a recessed slot 910, and bowl water 904. Recessed slot 910 is located above bowl water 904 and still low enough to trap urine in the slot 910. The slot 910 may comprise a trap region that traps urine via surface tension. The trap region may comprise a longitudinal dimension in a longitudinal direction and a transverse dimension in an orthogonal transverse direction, the longitudinal dimension being at least twice the transverse dimension. When urine measurements are complete, flush water release from toilet 900 may be used to clean trapped urine in area slot 910. Toilet flush patterns 908 and 906 may be formed to clean slot 910 when toilet 900 is flushed. A toilet controller may contain programming to wait for urine measurement devices to complete urine measurements before allowing the toilet to flush. For example, a user may push the flush button and a toilet controller may delay the flush until it receives acknowledgement that the urine measurements are complete.

Figure 10:
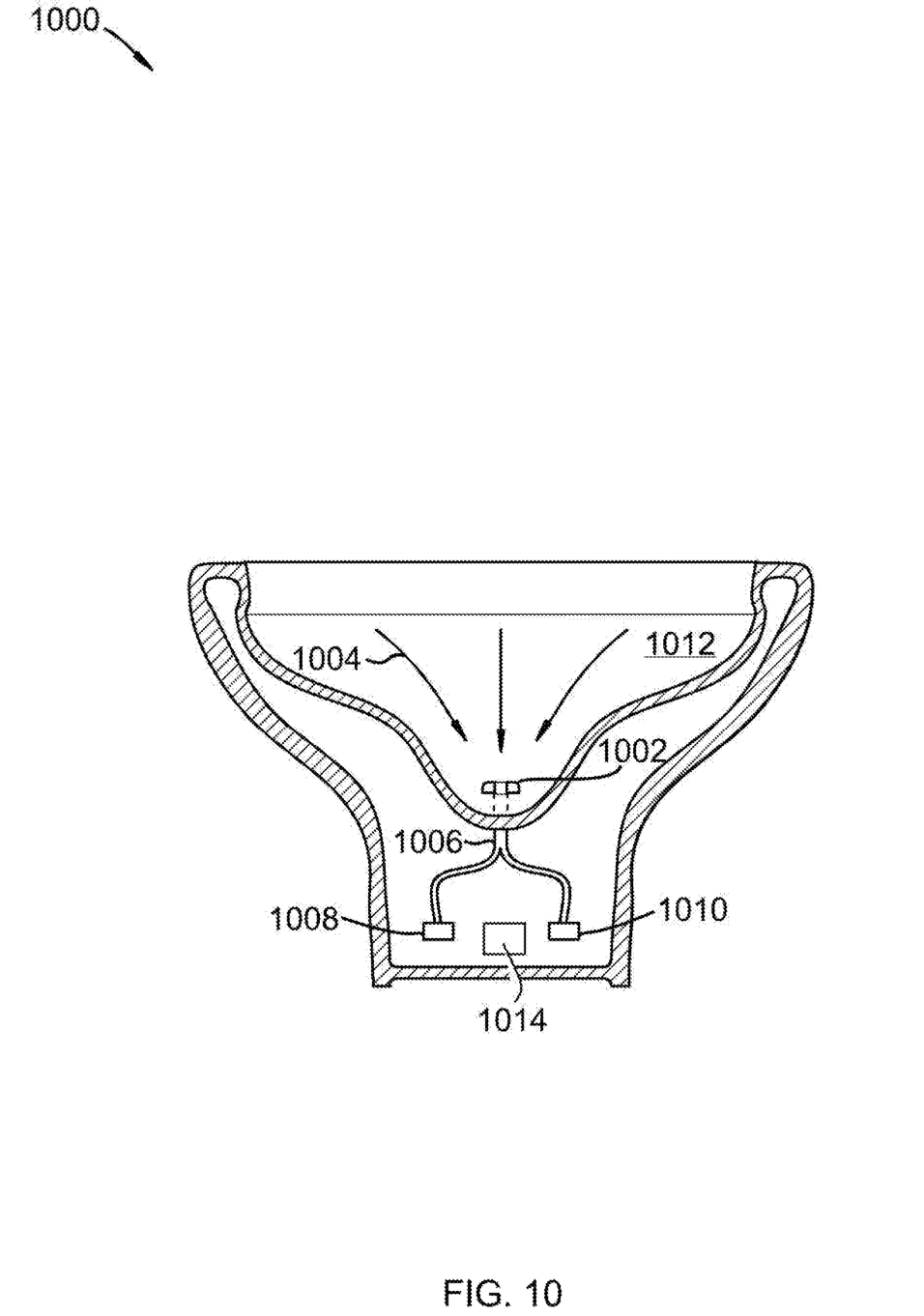
FIG. 10 shows a toilet bowl with urine measurement instruments.

Referring to FIG. 10, a toilet bowl 1000 with urine measurement instruments 1008 and 1010 is depicted with a urine trapping recess area 1002 and communication lines 1006. Measurement instruments 1010 and 1008 may comprise refractometers, spectrometers, glucose polarimeters, laser scatterometers, turbidity detectors, and/or microscopes. Measurement instruments 1010 and 1008 may each contain one or more controllers, processors, light sources, lenses, diffraction optics, collimating optics, power sources, and light detectors. Instrument controllers may be connected to a toilet controller 1014. The toilet controller may control measurement functions of instruments 1008 and 1010 in addition to flushing toilet 1000. Power sources may be battery power, generator power, or a wired power connection. Each controller may contain wireless and wired transceivers for communicating data to remote computers, user devices, and remote databases. Data may be communicated over the Internet or over local networks and devices. Urine trapping recess area 1002 may be formed by a slit, groove, recess, indentation, trench, pattern, divot, concavity, prism, lens, lens array, and/or diffraction grating. Communication lines 1006 may comprise wires or fiber optic lines.

Toilet bowl urine measurements may be taken when a toilet user urinates in toilet bowl 1012 and urine contacts urine trapping area 1002. The urine may directly hit trapping area 1002 as released by a toilet user or the urine may travel along an inside surface of toilet bowl 1012 and become trapped in area 1002. A temperature sensor may be located in trapping area 1002 may detect urine and trigger measurement devices 1010 and 1008 to measure urine trapped in area 1002. An inductive heater may be positioned within or near trapped area 1002. A toilet controller 1014 may preheat area 1002 and keep area 1002 at a fixed temperature while performing urine testing. When measurements are complete, flush water 1004 released from toilet bowl 1012 may be used to clean trapped urine in area 1002. A cleaning jet may be located above the recess. The cleaning jet may spray water, air, cleaning solution, or a combination thereof to clean and dry the recess. A cleaning solution may be used in combination with water, air, or a combination of water and air to clean the recess. A toilet controller 1014 may contain programming to wait for measurement devices 1010 and 1008 to complete urine measurements before allowing the toilet to flush 1004. For example, a user may push the flush button and a toilet controller 1014 may delay the flush until it receives acknowledgement that the urine measurements are complete.

The systems and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A toilet comprising:
   a bowl comprising:
   a recess configured to trap urine
   wherein the recess is in optical communication with a plurality of optical instruments;
   wherein the recess is formed by a slit, having an open top, open ends, side walls, and a base; and
   wherein the side walls at least partially comprise an optically transparent material and the base at least partially comprises an optically transparent material;
   a flush mechanism;
   one or more controllers;
   programming stored on the one or more controllers instructing the flush mechanism to wait for the plurality of optical instruments to complete a urine measurement before actuating the flush mechanism;
   wherein at least two of the plurality of optical instruments share a common light source and provide simultaneous measurements of the trapped urine in the recess; and
   wherein the plurality of optical instruments comprises a refractometer, a spectrometer, a glucose polarimeter, and a turbidity detector.

2. The toilet of claim 1, wherein the plurality of optical instruments includes at least two or more of: a laser scatterometer, a color detector, or a microscope.

3. The toilet of claim 1, wherein one or more of the plurality of optical instruments comprises an amplitude modulated light source.

4. The toilet of claim 1, wherein the at least two of the plurality of optical instruments share an amplitude modulated light source.

5. The toilet of claim 1, wherein the recess comprises a trap region that traps urine via surface tension, the trap region comprising a longitudinal dimension in a longitudinal direction and a transverse dimension in an orthogonal transverse direction, the longitudinal dimension being at least twice the transverse dimension; wherein the longitudinal dimension and the transverse dimension are orthogonal in a horizontal plane.

6. The toilet of claim 1, wherein the recess comprises a hydrophobic surface coating or a hydrophilic surface coating.

7. The toilet of claim 1, wherein the recess comprises a temperature sensor.

8. The toilet of claim 7, wherein the temperature sensor is configured to detect the urine entering the recess and to control a temperature of the recess.

9. The toilet of claim 7, wherein when the temperature sensor detects a change in temperature at least one of the plurality of optical instruments begins measuring the urine.

10. The toilet of claim 1, wherein two or more of the plurality of optical instruments share an optical path through the urine.

11. The toilet of claim 1, further comprising a beam splitter.

12. The toilet of claim 11, wherein the beam splitter is a polarization beam splitter.

13. The toilet of claim 1, wherein the one or more controllers are operably connected to one or more of the plurality of optical instruments.

14. The toilet of claim 1, further comprising a polarization beam splitter and a non-polarization beam splitter located on a common optical axis.

15. The toilet of claim 1, further comprising a heater in thermal communication with the recess.

16. The toilet of claim 1, wherein one or more of the plurality of optical instruments are glued to a surface of the bowl.

17. The toilet of claim 1, wherein the side walls of the recess consist of an optically transparent material.

18. The toilet of claim 1, wherein the base of the recess consists of an optically transparent material.

19. The toilet of claim 1 further comprising a longitudinal raised barrier wherein the recessed slit orthogonally traverses the barrier.

* * * * *